United States Patent
Blakley (10) Patent No.: US 7,558,621 B2
(45) Date of Patent: Jul. 7, 2009

(54) SYNTHESIZING A REFERENCE VALUE IN AN ELECTROCARDIAL WAVEFORM

(75) Inventor: Daniel Robert Blakley, Philomath, OR (US)

(73) Assignee: Hewlett-Packard Development Company, L.P., Houston, TX (US)

( * ) Notice: Subject to any disclaimer, the term of this patent is extended or adjusted under 35 U.S.C. 154(b) by 1080 days.

(21) Appl. No.: 10/758,813

(22) Filed: Jan. 16, 2004

(65) Prior Publication Data
US 2005/0159665 A1 Jul. 21, 2005

(51) Int. Cl.
*A61B 5/0402* (2006.01)
(52) U.S. Cl. ...................................... 600/509
(58) Field of Classification Search ................. 128/901; 600/509; 607/9
See application file for complete search history.

(56) References Cited

U.S. PATENT DOCUMENTS

| | | | |
|---|---|---|---|
| 3,868,567 A * | 2/1975 | Ekstrom | 600/517 |
| 4,446,868 A | 5/1984 | Aronson | |
| 4,545,380 A | 10/1985 | Schroeppel | |
| 5,503,159 A | 4/1996 | Burton | |
| 5,603,321 A * | 2/1997 | Kynor et al. | 600/409 |
| 5,615,687 A | 4/1997 | Pritchard | |
| 6,032,069 A | 2/2000 | Elgavish et al. | |
| 6,169,919 B1 * | 1/2001 | Nearing et al. | 600/518 |
| 6,324,421 B1 * | 11/2001 | Stadler et al. | 600/509 |

OTHER PUBLICATIONS

Ask; "ECG Electrodes, A Study of Electrical and Mechanical Long-term Properties"; Depts of Biomedical Eng & Dermatology, Sweden, Acta anaesth.scand. 1979, 23, pp. 189-206.

* cited by examiner

Primary Examiner—Angela D Sykes
Assistant Examiner—Rex Holmes (57) ABSTRACT

A method for synthesizing a reference value in an electrocardial waveform includes identifying a triggering event within the electrocardial waveform. The method also includes waiting a period of time after the triggering event until the electrocardial waveform enters an interval of relative inactivity, sampling the electrocardial waveform during the interval of relative inactivity, and referencing the electrocardial waveform to the sample.

15 Claims, 5 Drawing Sheets

SYNTHESIZING A REFERENCE VALUE IN AN ELECTROCARDIAL WAVEFORM

BACKGROUND OF THE INVENTION

In a clinical or a hospital setting, the cardiac functions of a patient may be monitored using several electrodes. In some settings, as many as 12 electrodes are used in order to provide accurate electrocardial information. Each of these electrodes must be properly affixed to the patient, often requiring a skilled practitioner to work for several minutes to affix each electrode. Not only can this be a time-consuming process, but also the resulting arrangement of affixed electrodes restricts the patient's movement as well as being both uncomfortable and annoying to the patient. Thus, patients who require frequent cardiac monitoring may become further disinclined to see the doctor. Further, in a home health care environment, the need for numerous electrodes makes home health care monitoring equipment complicated and inconvenient to use.

Typically, several electrodes are affixed to various chest locations on the patient in order to record the electrocardial information. Further, at least one reference electrode is placed at a location where electrical activity is minimal, such as on one of the patient's lower legs. When the reference electrode is affixed to a patient's lower leg, the reference electrode can be especially annoying since the electrode restricts the patient's ability to walk or even wear trousers without stressing the electrode and the skin at which the electrode is attached.

DESCRIPTION OF THE EMBODIMENTS

Figure 1:
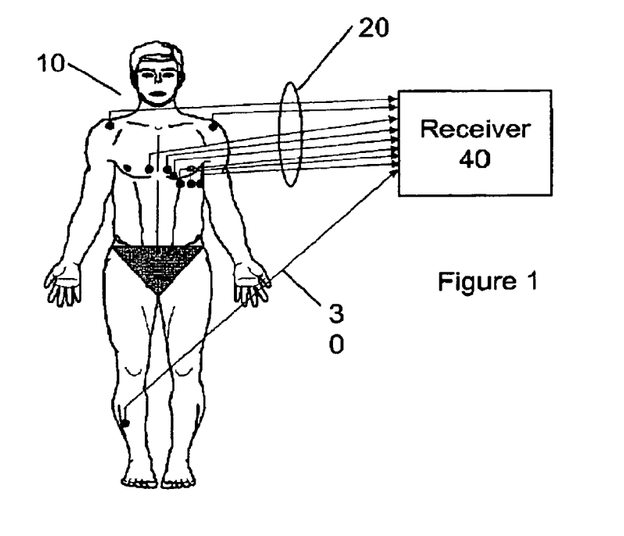
FIG. 1 is a diagram of a patient having several electrodes affixed to the chest and a reference electrode attached to the patient's leg.

FIG. 1 is a diagram of a patient (10) having several electrodes (20) affixed to the chest and a reference electrode attached to the lower leg. Signal electrodes 20 convey time-varying voltages that represent the electrocardial waveform of the patient to receiver 40. Additionally, reference electrode 30, attached to the lower leg of patient 10, provides a stable reference signal to which the time-varying electrical voltages present on signal electrodes 20 can be compared. The use of reference electrode 30 allows receiver 40 to mitigate the effects of noise or other stray voltages that may be coupled onto signal electrodes 20 and reference electrode 30.

Figure 2:
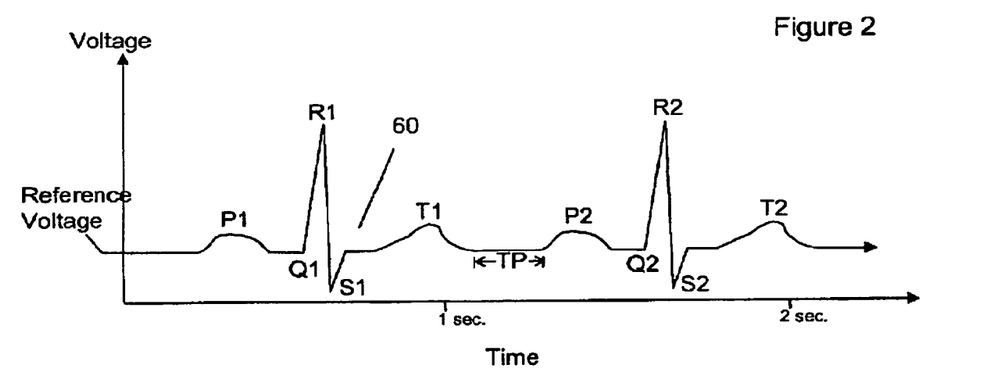
FIG. 2 represents a typical electrocardial waveform showing various electrocardial events.

FIG. 2 represents a typical electrocardial waveform showing various electrocardial triggering events as well as intervals of relative inactivity. In accordance with conventional notations, a P wave (shown as P1 in FIG. 2) is the first event of the sinus rhythm, indicating atrial depolarization. The P wave is followed by a short interval of relative inactivity, followed by the onset of the QRS complex (shown as Q1, R1, and S1 in FIG. 2), during which the ventricles are depolarized. After the QRS complex, a second interval of relative inactivity occurs prior to the onset of the T wave (shown as T1 in FIG. 2), during which the ventricles are repolarized. At the conclusion of the T wave (shown as T1 in FIG. 2), a third interval of relative inactivity, the TP interval, occurs prior to the onset of the P wave of a second and subsequent electrocardial waveform (shown as P2, Q2, R2, S2, and T2 in FIG. 2). In FIG. 2, during each interval of relative inactivity, the amplitude of the electrocardial waveform is shown as returning to a reference voltage value. This reference voltage value is generally contemplated as being zero volts (ground).

The horizontal axis of FIG. 2 shows a time scale that is approximately 2 seconds in length, consistent with the timing of a normal sinus rhythm of a human heart beating at a rate of 60 beats/minute. Although an entire electrocardial waveform (including 1 P wave, 1 QRS complex, and 1 T wave) occurring in a time frame of about 1 second, physical exertion and other factors may cause the heart rate to increase. However, during these periods of increased heart rate, the character and shape of the above-described electrocardial events can be expected to remain unchanged.

Figure 3A:
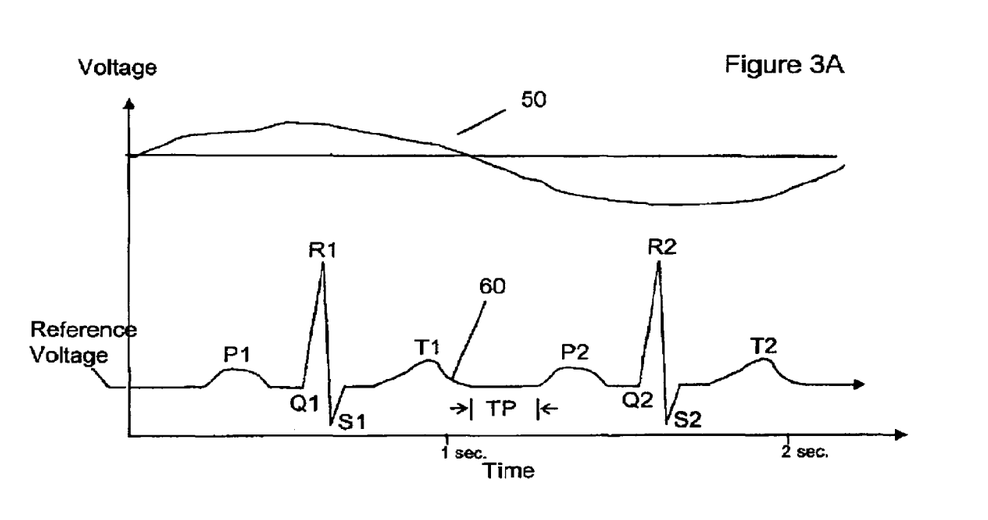
FIG. 3A shows a noise signal having an amplitude and time scale that accords with the electrocardial waveform of FIG. 2.

FIG. 3A shows a noise signal having an amplitude and time scale that accords with the electrocardial waveform of FIG. 2. In FIG. 3A, noise signal 50 represents a roughly sinusoidal stray voltage coupled onto one or more of the signal electrodes. In one embodiment, noise signal 50 represents a signal that corresponds to an alternating current used in a household or hospital environment. However, noise signal 50 may include significant frequency components in addition to an alternating current waveform.

From FIG. 3A, it can be seen that noise signal 50 represents a signal having frequency components in the same range as those of electrocardial waveform 60. Thus, noise signal 50 cannot easily be filtered by way of conventional low pass filtering techniques without distorting electrocardial waveform 60. Further, since typical voltages of the electrocardial waveforms when measured on the patient tend to be on the order of 5 to 10 millivolts at currents of less than 20 microamperes, these waveforms can be susceptible to radiated or conducted noise signals that may be coupled either directly onto patient 10 or onto one or more of signal electrodes 20.

Figure 3B:
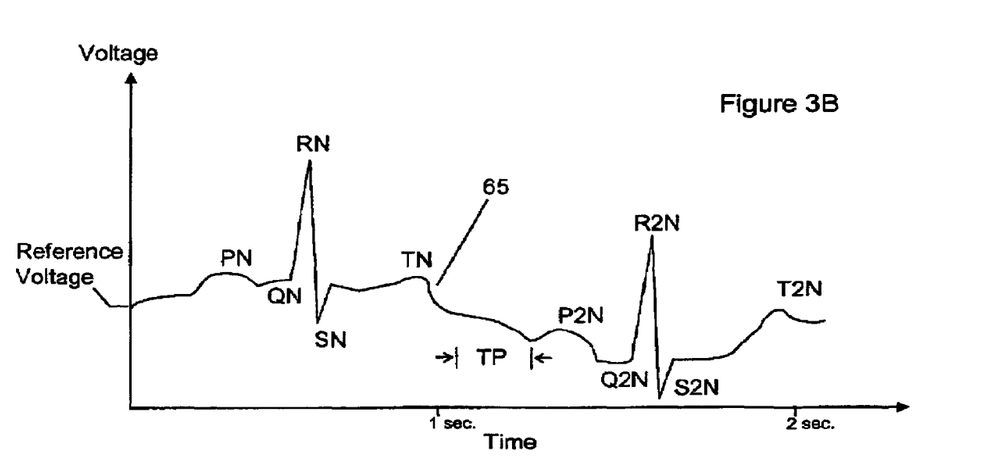
FIG. 3B shows the noise signal and the electrocardial waveform of FIG. 3A added together to form a noisy electrocardial waveform.

FIG. 3B shows the noise signal and the electrocardial waveform of FIG. 3A added together to form noisy electrocardial waveform 65. Thus, the presence of the noise signal modifies the intervals of relative electrical inactivity (of FIG. 2) so that these intervals now exhibit increased activity. In FIG. 3, the triggering events such as the P1 wave, the Q1R1S1 complex, and the T1 wave have been replaced by a PN wave, a QNRNSN wave, and a TN wave to denote the presence of noise superimposed onto the triggering event.

Figure 4:
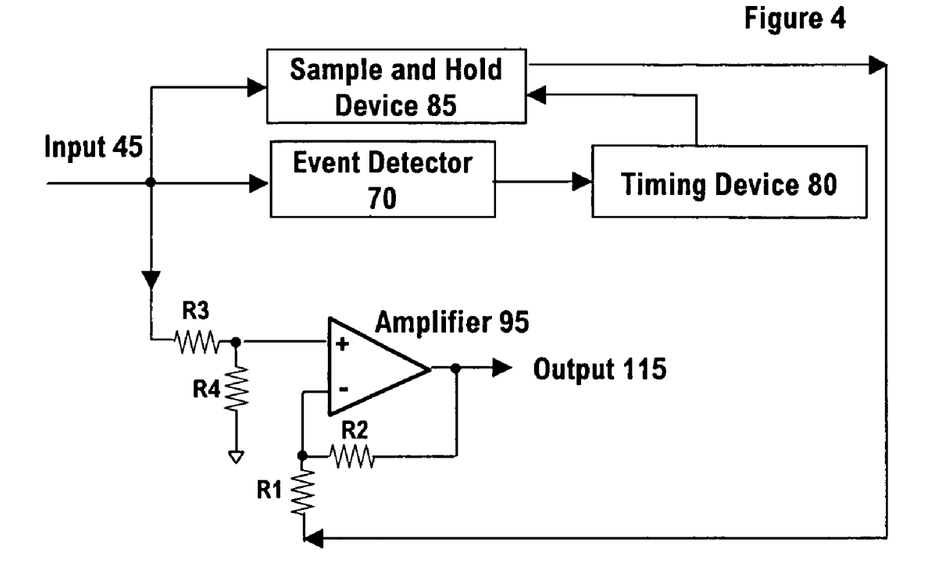
FIG. 4 shows a reference voltage generating circuit that supplants the reference electrode according to an embodiment of the invention.

FIG. 4 shows a reference voltage-generating circuit that supplants the reference electrode according to an embodiment of the invention. In FIG. 4, an electrode input 45 conveys an electrical voltage from one or more electrodes affixed to a patient's chest. Not shown in FIG. 4 is an instrumentation amplifier that may provide on the order of 80 dB of common mode rejection. However, although the amplifier may have a substantial ability to reject common mode signals, differential mode noise voltages (that is, voltage signals not common to two or more inputs) are amplified along with the signals that represent the electrocardial waveform. Further, common mode signals of higher amplitudes are also amplified such that even 80-100 dB of common mode rejection may not be sufficient to adequately reduce the level of noise coupled onto electrode input 45.

The signal from electrode input 45 is conveyed to event detector 70, which detects the peak of one or more of the P wave, the QRS complex, and the T wave of the electrocardial waveform In the embodiment of FIG. 4, when event detector 70 detects the peak of the QRS complex of the electrocardial waveform, timing device 80 is placed in a waiting state until the electrocardial waveform can be expected to enter an interval of relative inactivity. For a sinus rhythm of 1 heartbeat per second (for example), timing device 80 waits approximately 0.6 or 0.7 seconds until the onset of interval TP. At the onset of sample and hold interval TP, sample and hold device 85 samples the value of the input electrocardial waveform. The sampled value of the waveform is then held at the output of sample and hold device 85 and conveyed to the inverting input of amplifier. The voltage sampled during the expected period of relative inactivity can then be subtracted from electrode input 45 according to the well-known subtractive transfer function of the summing amplifier of FIG. 4:

$$V_{Output\ 115} = R2/R1(V_+ - V_-)$$

Wherein the values for R1, R2, R3, and R4 are selected such that R2/R1=R4/R3, and wherein $V_+$ denotes the noninverting input (+) of amplifier 95, and wherein $V_-$ denotes the inverting input of the amplifier.

Thus, the embodiment of FIG. 4 provides a periodic correction to the input electrocardial waveform. Upon the detection of the peak of the QRS complex, timing device 80 measures an amount of time after which the electrocardial waveform can be expected to be electrically inactive. During each interval of relative electrical inactivity, sample and hold device 85 provides amplifier 95 with a reference voltage to which the signal of input 45 can be compared. This allows the various triggering events of the electrocardial waveform to be measured relative to the reference voltage.

In alternate embodiments, event detector and timing device 80 can be programmed to trigger sample and hold device 85 in response to various other events of the electrocardial waveform. Thus, in another embodiment, event detector 70 can respond to the peak of the P wave, while timing device 80 activates sample and hold device 85 in the interval that precedes the QRS complex. Further, after detecting the R peak of the QRS waveform, sample and hold device 85 can sample the incoming waveform prior to the onset of the T wave. These additional samplings of the incoming signal (from electrode input 45) allow sample and hold device 85 to provide additional voltages to the inverting input of amplifier 95, thus allowing the more frequent subtraction of noise from the incoming electrocardial waveform. This, in turn, provides a more accurate electrocardial waveform measurement even though significant noise may be present in the incoming signal. Further, the periodic corrective action functions to maintain the input signal within the operative range of the amplifier 95, thereby allowing the predictable operation of the amplifier by correcting for DC wander and other low-frequency noise phenomena.

Figure 5:
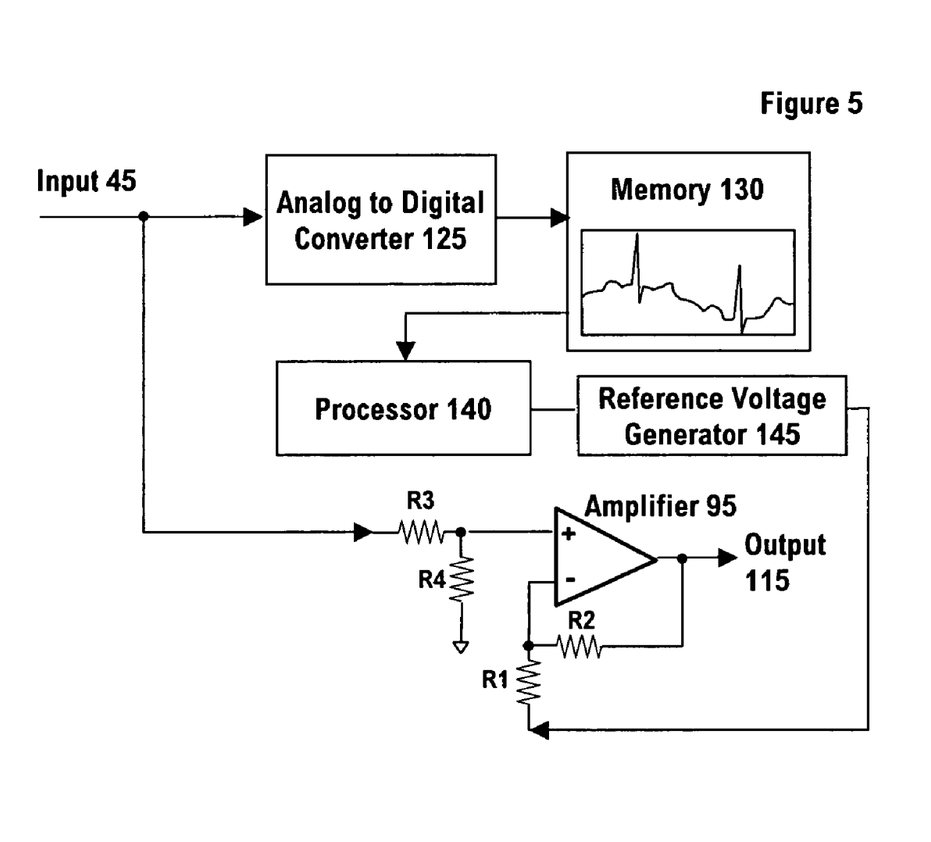
FIG. 5 shows a memory and processor replacing the event detector, timing device, and sample and hold device of FIG. 4 according to an embodiment of the invention.

FIG. 5 shows a memory and processor replacing the event detector, timing device, and sample and hold device of FIG. 4 according to an embodiment of the invention. In FIG. 5, electrode input 45 is input to memory 130 by way of analog to digital converter 125. Memory 130 represents a memory array capable of storing several electrocardial waveforms recorded in succession. Thus, although only one or two complete electrocardial waveforms are shown as being stored in memory 130, embodiments of the present invention can include the capability for memory 130 to store several waveforms recorded over several seconds or longer.

The use of memory 130 and processor 140 may provide increased flexibility in the selection of triggering events used to establish periods of relative inactivity. Thus, processor 140 may detect the R peak of the QRS complex followed by a period of 0.2 seconds (for example) before sampling the waveform to determine the voltage that should be subtracted from the waveform by way of amplifier 95. During periods of increasing or decreasing cardiac activity, such as during or after vigorous exercise by the patient, processor 140 may measure successive peak R-values to determine the current heart rate and correspondingly adjust the time period before which the waveform is sampled. Further, processor 140 may determine that the incoming waveform includes one or more of a P wave, a period of relative inactivity, a QRS complex that includes a positive R peak, a second period of relative inactivity, a T wave, and a third period of relative inactivity prior to the onset of a the P wave of a subsequent waveform. Any of the aforementioned events can be used to trigger the sampling of the incoming waveform.

The use of memory 130 and processor 140 allow the incoming waveform to be sampled more than once during a given period of relative inactivity. Thus, for the waveform of FIG. 3B, the incoming waveform may be sampled more than once during the TP interval to determine the rate of change in the voltage of the waveform. These additional samples, as well as the rate of change in the voltage during the sampling interval, may be used to better estimate (such as by averaging or extrapolating) the reference voltage generated by processor 140 and presented to the inverting input of amplifier 95.

Returning to FIG. 5, processor 140 searches for the various triggering events within the electrocardial waveform stored in memory 130. Upon the detection of an appropriate triggering event, such as the R peak of a QRS complex, processor 140 outputs a value to reference voltage generator 145. Reference voltage generator 145 provides a voltage to the inverting input of amplifier 95. Amplifier 95 then subtracts the reference voltage from the incoming signal. In a manner that accords with the circuit of FIG. 4, some embodiments of the invention may include processor 140 selecting additional intervals where electrical inactivity can be expected to occur. During these intervals, the digitized version of the incoming waveform can be sampled. The sampled values can then be used to adjust the output of reference voltage generator 90, thereby subtracting noise from the incoming signal.

Although the subtraction function could be performed almost entirely by way of processor 140, without the use of amplifier 95, performing the subtraction in the analog domain maintains the input signal within the linear range of the amplifier.

In addition to responding to triggering events solely in response to events in the time domain, processor 140 may perform a linear transform (such as a Fourier transform) so that frequency information can be used to determine that a particular triggering event has occurred. Thus, when higher frequency components are detected, processor 140 may determine the presence of an R peak of the QRS complex in an incoming electrocardial waveform. When lower frequency components are detected, the processor may determine that either a P wave or a T wave is present. Thus, in some embodiments, the use of frequency information can be coupled with time domain information to produce a more accurate indication of a triggering event.

Figure 6:
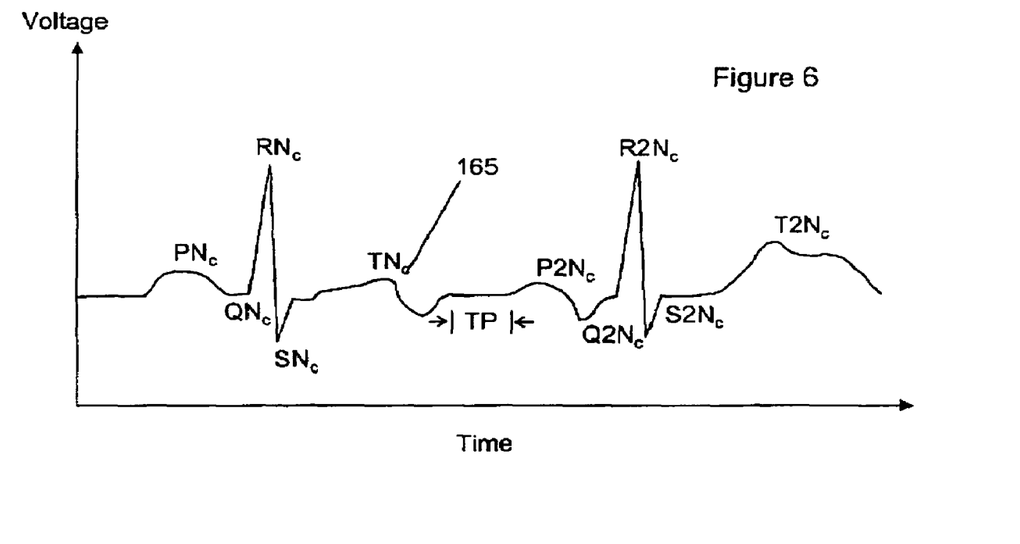
FIG. 6 shows the noisy electrocardial waveform of FIG. 3B after a substantial portion of the noise have been subtracted from the incoming waveform according to an embodiment of the invention.

FIG. 6 shows the noisy electrocardial waveform of FIG. 3B after a substantial portion of the noise have been subtracted from the incoming waveform according to an embodiment of the invention. In FIG. 6, corrected waveform 165 includes each of the events of FIG. 3B, such as PN, QN, RN, and so forth, has been renamed with a subscript "c" to denote that the waveform has been corrected by way of one of circuits 4 and 5. Thus, although the waveform of FIG. 6 may still exhibit some distortion, waveform 165 includes much less noise the waveform of FIG. 3B.

Figure 7:
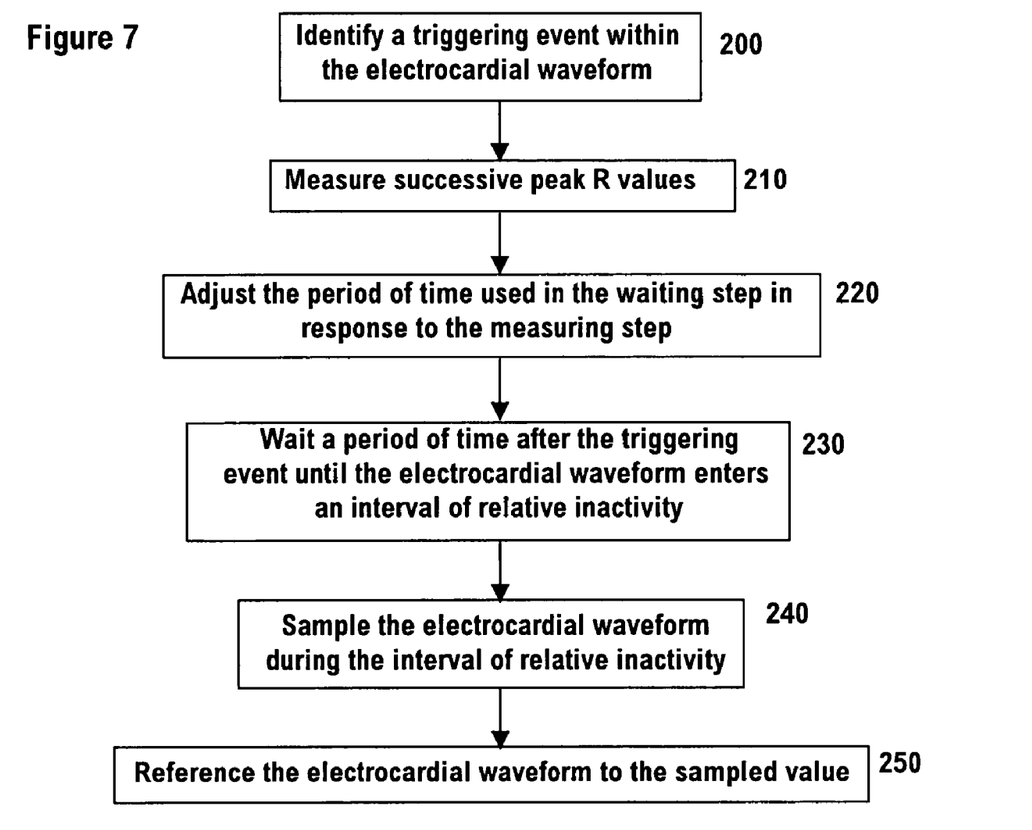
FIG. 7 is a flowchart for a method of synthesizing a reference value in an electrocardial waveform according to an embodiment of the invention.

FIG. 7 is a flowchart for a method of synthesizing a reference value in an electrocardial waveform according to an embodiment of the invention. The apparatus of FIGS. 4 or 5 are suitable for performing the method of FIG. 7. The method of FIG. 7 begins at step 200, in which a triggering event in the incoming electrocardial event is identified. In one embodiment, the triggering event is a positive peak R-value in the QRS complex of the electrocardial waveform followed by a negative peak (S) in the QRS complex. In another embodiment, the positive peak R-value is followed by a period of relative inactivity (such as 0.2 seconds) and then followed by a T wave. The method continues at step 210, at which successive peak R-values are measured, thus allowing a previously recorded electrocardial waveform to be used to determine an interval of relative inactivity of a subsequently-recorded electrocardial waveform. At step 220 the period of time used in the waiting step (of step 230) is adjusted in response to the measuring step.

The method continues at step 230, which includes waiting a period of time after the triggering event until the electrocardial waveform enters an interval of relative inactivity, such as during the PT interval. In the embodiment of FIG. 7, the waiting period corresponds to the period adjusted in step 220. The method continues at step 240, in which the electrocardial waveform is sampled during the interval of relative inactivity. Step 240 may also include the step of supplying a reference voltage that is substantially equal to the value of the sampled voltage, such as by way of a sample and hold device.

The method continues at step 250 in which the electrocardial waveform 250 is referenced to the sampled value. This may include the subtraction of the sampled value from the incoming waveform, such as is performed by amplifier 95 of FIGS. 4 and 5. It is contemplated that the referenced value supplants the ground provided by reference electrode 30 (such as shown in FIG. 1).

Some embodiments of the invention may only include the steps of identifying a triggering event within the electrocardial waveform (step 200), waiting a period of time after the triggering event until the electrocardial waveform enters an interval of relative inactivity (step 230), sampling the electrocardial waveform during the interval of relative inactivity (step 240), and referencing the electrocardial waveform to the sample (step 250). In another embodiment of the invention, only the steps of identifying a triggering event within the electrocardial waveform (step 200), sampling the electrocardial waveform during the interval of relative inactivity (step 230), and referencing the electrocardial waveform to the sample are performed (step 250).

The method of FIG. 7 may be encoded in a computer-readable media, such an optical disk, flash memory card, or other removable storage media having computer-readable instructions thereon, which, when executed by a computer, cause the computer to synthesize a reference value for an electrocardial waveform. The computer readable media may also be a hard disk or other storage media internal to the computer or to a computing device (such as a personal digital assistant) that executes programs loaded from the removable media or downloaded to the computer by way of the public Internet or downloaded from a private network. In any event, the computer readable media includes computer-readable media includes instruction which, when executed by a computer, cause the computer to perform the method.

While the present invention has been particularly shown and described with reference to the foregoing preferred and alternative embodiments, those skilled in the art will understand that many variations may be made therein without departing from the spirit and scope of the invention as defined in the following claims. This description of the invention should be understood to include all novel and non-obvious combinations of elements described herein, and claims may be presented in this or a later application to any novel and non-obvious combination of these elements. The foregoing embodiments are illustrative, and no single feature or element is essential to all possible combinations that may be claimed in this or a later application. Where the claims recite "a" or "a first" element of the equivalent thereof, such claims should be understood to include incorporation of one or more such elements, neither requiring nor excluding two or more such elements.

What is claimed is:

1. A method for applying a reference value to an electrocardial waveform including a series of heart beats, the method comprising:
  identifying a triggering event within the electrocardial waveform;
  waiting a period of time after the triggering event for an interval of relative inactivity in the waveform;
  sampling the electrocardial waveform during the interval of relative inactivity to provide a sample voltage value corresponding to a selected beat; and
  dynamically referencing the electrocardial waveform to the sample voltage value over a period of the selected beat.

2. The method of claim 1, wherein the interval of relative inactivity occurs during a TP interval of the electrocardial waveform.

3. The method of claim 1, wherein the triggering event is a peak R-value in a QRS complex of the electrocardial waveform.

4. The method of claim 1, wherein the triggering event is a peak R-value in a QRS complex of the electrocardial waveform followed by at least one of a negative S peak in the QRS complex and a T wave.

5. The method of claim 1, wherein the triggering event is a peak R-value in a QRS complex followed by a period of at least 0.2 seconds of relative inactivity.

6. The method of claim 1, further comprising measuring a value of the interval of relative inactivity between successive peak R values and modifying the length of the period of time waiting in response to the measured interval values.

7. The method of claim 1, wherein the sample voltage value supplants a ground provided by a reference electrode used in recording the electrocardial waveform.

8. The method of claim 1, wherein referencing the electrocardial waveform includes supplying a reference voltage substantially equal to the value of the sampled waveform during the interval of relative inactivity.

9. The method of claim 1, wherein identifying the triggering event additionally comprises detecting frequency components in the electrocardial waveform.

10. A system for generating a reference value for an electrocardial waveform including a series of beats, comprising:
- at least one electrode input that conveys a voltage signal of the electrocardial waveform of a patient;
- an event detector that detects an event within the electrocardial waveform;
- a sampling device that determines the reference value corresponding to a selected beat;
- a timing device that, after a wait period in response to the event detector, activates the sampling device; and
- a referencing element that applies the reference value to the voltage signal over a period of the selected beat.

11. The system of claim 10, wherein the reference value is substantially zero volts.

12. The system of claim 10, wherein the event is an R peak of a QRS complex of the eleotrocardial waveform.

13. The system of claim 10, wherein the event is an interval of relative inactivity followed by a peak of a QRS complex of the electrocardial waveform.

14. The system of claim 10, wherein the sampling device measures a rate of change in the voltage signal of the electrocardial waveform, and determines the reference value based at least in part on the rate of change in the voltage signal.

15. The system of claim 10, further comprising a processor, coupled to the timing device, configured to measure the time between successive corresponding events in the electrocardial waveform and to modify a length of the wait period in response to the measured time.

* * * * *

UNITED STATES PATENT AND TRADEMARK OFFICE
CERTIFICATE OF CORRECTION

| | | |
|---|---|---|
| PATENT NO. | : 7,558,621 B2 | Page 1 of 1 |
| APPLICATION NO. | : 10/758813 | |
| DATED | : July 7, 2009 | |
| INVENTOR(S) | : Daniel Robert Blakley | |

It is certified that error appears in the above-identified patent and that said Letters Patent is hereby corrected as shown below:

In column 8, line 2, in Claim 12, delete "eleotrocardial" and insert -- electrocardial --, therefor.

Signed and Sealed this

Sixteenth Day of March, 2010

David J. Kappos
*Director of the United States Patent and Trademark Office*